US006436678B2

(12) United States Patent
Antrim et al.

(10) Patent No.: US 6,436,678 B2
(45) Date of Patent: Aug. 20, 2002

(54) HIGH PURITY MALTOSE PROCESS AND PRODUCTS

(75) Inventors: Richard L. Antrim, Solon; Clark P. Lee, Blue Grass, both of IA (US)

(73) Assignee: Grain Processing Corporation, Muscatine, IA (US)

( * ) Notice: Subject to any disclaimer, the term of this patent is extended or adjusted under 35 U.S.C. 154(b) by 0 days.

(21) Appl. No.: 09/796,027

(22) Filed: Feb. 28, 2001

Related U.S. Application Data

(60) Provisional application No. 60/185,474, filed on Feb. 28, 2000.

(51) Int. Cl.$^7$ .................................................. C12P 19/22
(52) U.S. Cl. ............................ 435/95; 435/72; 435/99; 435/100; 536/123.13; 127/38; 127/40
(58) Field of Search ............................ 435/95, 99, 100, 435/72; 536/123.13; 127/40, 38

(56) References Cited

U.S. PATENT DOCUMENTS

| | | |
|---|---|---|
| 3,705,039 A | 12/1972 | Mitsuhashi et al. |
| 3,795,584 A | 3/1974 | Mitsuhashi et al. |
| 3,804,715 A | 4/1974 | Sugimoto et al. |
| 3,832,285 A | 8/1974 | Kurimoto et al. |
| 4,001,435 A | 1/1977 | Hirao et al. |
| 4,028,186 A | 6/1977 | Sakai |
| 4,032,403 A | 6/1977 | Sakai et al. |
| 4,487,198 A | 12/1984 | Miyake et al. |
| 4,511,654 A | 4/1985 | Rohrbach et al. |
| 4,780,149 A | 10/1988 | Kaper et al. |
| 4,816,445 A | 3/1989 | Mitsuhashi et al. |
| RE33,047 E | 9/1989 | Miyake et al. |
| 4,977,252 A | 12/1990 | Chiu |
| 5,112,407 A | 5/1992 | Sakai et al. |
| 5,185,176 A | 2/1993 | Chiu |
| 5,482,560 A | 1/1996 | Ammeraal et al. |
| 5,562,937 A | 10/1996 | Senkeleski et al. |

FOREIGN PATENT DOCUMENTS

| | | |
|---|---|---|
| EP | 0 242 913 A3 | 10/1987 |
| EP | 0 332 027 A1 | 9/1989 |
| EP | 1 016 728 A2 | 7/2000 |
| WO | WO 95/10627 | 4/1995 |
| WO | WO 01/16348 A1 | 3/2001 |
| WO | WO 01/16349 A1 | 3/2001 |

OTHER PUBLICATIONS

Peat et al, J. Chem. Soc. 1952:705–713.*
Sugimoto et al., "Manufacture of Maltose with Yeats," Patent Abstract (JP 05219977) (1993).
Takahashi et al., "Manufacture of High Purity maltose Aqueous Solutions," Patent Abstract (JP 04271793) (1992).
Maruo et al., "A Novel and Efficient Method for Enzymic Synthesis of High Purity Maltose Using Moranoline (1–Deoxynojirimycin)," Chem. Lab., 56(9), 1406–1409 (1992).
Nehete et al., "An Optimized Protocol for the Production of High Purity Maltose," Worl J. Microbol, Biotechnol, 8(4), 446–450 (1992).
Niimi et al., "Enzymic Manufacture of High–Purity Maltose from Starch," Patent Abstract (JP 04158795) (1992).
Niimi et al.,, "Preparation of High–Purity Maltose by Crystallization," Patent Abstract (JP 03228688) (1991).
Niimi et al., "Enzymic Manufacture of Highly Pure Maltose and its Hydrolyzate," Patent Abstract (JP 02092296) (1990).
Niimi et al., "Maltose Having High–Purity and its Manufacture,"Patent Abstract (JP 02119789) (1990).
Sakai et al., "Process for Preparing Maltose Powder," Patent Abstract (EP 88–304743) (1988).
Goodman, "Process for Separating Maltose from Mixtures of Maltose, Glucose and Other Saccharides," Patent Abstract (U.S. 4,707,190) (1987).
Takasaki, "High Maltose Preparation," Patent Abstract (JP 60186296) (1985).
Miyake et al., "High Purity Maltose," Patent Abstract (FR 2510581) (1983).
Walon, "Maltose–Containing Starch Hydrolyzate and Crystallization of Maltose Therefrom," Patent Abstract (U.S. 4,199,372) (1980).
Konishi et al., "Maltase Having High Purity," Patent Abstract (JP 53118532) (1978).
Okada et al., "Maltose of High Purity," Patent Abstract (JP 7757344) (1977).
Takasaki, "High Purity Maltose," Patent Abstract (JP 7707487) (1977).
Takasaki, "High Purity Maltose," Patent Abstract (JP 7707486) (1977).
Yabuki et al., "Preparing Maltose," Patent Abstract (JP 76101141) (1976).
Murayama et al., "Maltose," Patent Abstract (JP 7698346) (1976).
Sakai, "Starch–Saccharified Product Having High Maltose–Purity," Patent Abstract (JP 51070833) (1976).
Mitsuhashi, "Production of Very Pure Maltose from Starch," Patent Abstract (FR 2012831) (1970).
Mitsuhashi, "High–Purity Maltose from Starch," Patent Abstract (ZA 6904923) (1970).
Kurimoto et al., "Highly Pure Crystalline Maltose from Starch," Patent Abstract (DE 1958014) (1970).
Hayashibara Co., Ltd., "High–Purity Maltose," Patent Abstract (JP 19670630) (1969).
Sugimoto et al., "High–Purity Maltose by Removing Contaminating Glucose with Yeast," Patent Abstract (JP 61104794) (1986).

(List continued on next page.)

Primary Examiner—Francisco Prats
(74) Attorney, Agent, or Firm—Leydig, Voit & Mayer Ltd.

(57) ABSTRACT

Maltose products are prepared by hydrolyzing starch with an enzyme that consists essentially of a beta-amylase enzyme. The product thus prepared may be spray dried, or a high purity maltose product may be obtained therefrom via ultrafiltration. The high purity maltose product has a low content of glucose and saccharides in the DP 3–10 range.

14 Claims, No Drawings

OTHER PUBLICATIONS

Akio et al., "Studies on Production of Maltose by Membrane Separation Technique," Chemical Abstracts Service, DN 93:148430 (XP–002177602) (1979).

Ghiasi et al., "Note on the Hydrolysis of Amylose by Beta–Amylase," Starch/Stärke, Dep. of Grain Sci. & Ind., Kansas State Univ., 33 (12), pp. 428–430 (XP–002177601) (1981).

Database CA Online Chemical Abstracts Service, Columbus Ohio, US: Taki Akio Et Al: "Studies on production of maltose by membrane separation technique" retrieved from STN Database accession No. 93:148430 XP002177602 abstract & Shokuhin Sangyo Senta Gijutsu Kenkyu Hokoku (1979), 3, 13–23.

* cited by examiner

HIGH PURITY MALTOSE PROCESS AND PRODUCTS

RELATED APPLICATION

This application claims priority to prior provisional application Ser. No. 60/185,474 filed on Feb. 28, 2000, the entire contents of which are hereby incorporated by reference.

TECHNICAL FIELD OF THE INVENTION

This invention is in the field of oligosaccharides, and in particular, the invention pertains to the preparation of a high-purity maltose product.

BACKGROUND OF THE INVENTION

Maltose, an alpha 1–4 linked disaccharide, is a commercially important chemical with numerous industrial and consumer uses, for instance, as a sweetener or in the preparation of maltitol, a different sweetener in confectioneries intended for the low calorie or diabetic market. Maltose is also commercially important in the brewing industry, wherein it is provided as a fermentable component of brewing worts. In these applications, it is desirable to provide maltose in a substantially pure form, i.e., to the substantial exclusion of other carbohydrates. For instance, it is desirable in brewing applications to provide maltose to the substantial exclusion of dextrose. Although dextrose is fermentable, dextrose begins to inhibit yeast growth when present in the brewing wort, for reasons believed to relate to metabolic disturbances of the yeast used in the fermenting process. Similarly, in the preparation of maltitol, it is commercially desirable to provide maltose in a substantially pure form, so that sorbitol and higher molecular weight hydrogenated sugars such as maltotritol are not formed upon hydrogenation of the maltose. For these reasons, the production of maltose in a highly pure form is highly commercially desirable. It is particularly desirable to avoid substantial amounts of glucose, maltotriose, or other lower molecular weight sugars, because of the difficulty in separating maltose from such other carbohydrates.

Generally, maltose is prepared via the enzymatic hydrolysis of starch, whereby certain enzymes, known as beta amylases, convert starch into maltose. Natural starches are composed of two molecules, amylose, a linear saccharide, and amylopectin, a branched starch molecule which for a given starch ordinarily is of higher molecular weight than amylose and in which approximately 4% of the glucoside bonds are alpha 1–6 bonds. With the exception of so-called waxy (corn) or glutinous (rice) specialty starches, most starches found in nature are composed of between 20% and 30% amylose. In the case of amylose, beta-amylase enzymes catalyze hydrolysis from the non-reducing end of the molecule, thus releasing maltose units sequentially until the reducing end is reached. Presumably, if the amylose molecule contains an even number of glucose units, the sole product will be maltose; however, if the amylose molecule contains an odd number of glucose units, then, in addition to maltose, one glucose molecule is released per amylose molecule from the reducing end. In addition to glucose, maltotriose is often seen as an end product due to the relatively slow conversion of maltotriose to glucose and maltose. Moreover, if the amylose were present as a large number of short molecules, such as would be the case if the amylose had been partially hydrolyzed with an acid or alpha-amylase enzyme, then relatively larger amounts of glucose and maltotriose would result upon treatment of the short-chain amylose with beta-amylase. With respect to amylopectin, beta-amylase enzymes release maltose by sequential hydrolysis, but when the sequential hydrolysis reaches an alpha 1–6 branch point, the hydrolysis stops because the enzyme is unable to hydrolyze the branch point. As a result, the highest yield of maltose obtainable from amylopectin is about 50%. The remaining 50% of the original amylopectin exists as large, essentially water-soluble molecules.

For the foregoing reasons, the purity of the maltose product obtained via enzymatic hydrolysis of a starch is related to the number of amylose molecules per given weight of starch, and is limited by the extent of branching in the amylopectin component of the starch. Because of the production of by-products such as glucose and maltotriose, it is difficult to obtain a high-purity maltose from starch without subsequent purification steps. Conventionally, chromatographic processes have been employed to separate maltose from the glucose and other by-products of the beta-amylase hydrolysis product. Chromatographic separations are expensive and difficult to perform, however, thus resulting in an increased cost for a high-purity maltose product.

In recognition of this problem, the prior art has provided a number of attempts to improve the yield of maltose from starch. For instance, yields of maltose from amylopectin can be significantly increased by cleaving (hydrolyzing) the amylopectin structure between branch points with acid or with an alpha-amylase enzyme. This can be done either before treating the starch with a beta-amylase enzyme, or concurrently therewith. By cleaving between branch points, additional non-reducing ends are produced, thus providing more sites for attack by the beta-amylase enzyme. Using this technique, yields of maltose can be increased, but in addition to maltose, small branched molecular products undesirably are produced. Another strategy for increasing yields of maltose for amylopectin is the use of enzymes that hydrolyze the alpha 1–6 branch points. Enzymes such as pullulanse and isoamylase are known; such enzymes are generally known as alpha 1–6 glucosidases.

Such techniques are somewhat effective in improving the yield of maltose. For example, if normal starch (containing about 25% amylose and 75% amylopectin) is liquefied using conventional alpha-amylase or acid liquefaction techniques, and then treated with barley beta-amylase, a yield of about 55% maltose can be expected, the yield depending somewhat on the extent of prior hydrolysis with alpha-amylase. Barley malt-derived beta-amylase enzymes, which contain an alpha-amylase component, will provide a maltose yield of closer to 60%. The use of starch de-branching enzymes will provide even higher yields, ranging up to 75% maltose. Other attempts have focused on the development of new enzymes for use in the production of maltose from starch. One such enzyme (Maltogenase, from Novozymes A/S) is used in combination with an alpha-amylase enzyme, a beta-amylase enzyme, and a pullulanse enzyme to obtain maltose from starch. The maximum yield of maltose using these four enzymes appears to be about 80%.

The use of multiple enzymes on a commercial scale is expensive, both in connection with the purchase of such enzymes and the removal of the enzymes from the maltose product thus prepared. In addition, although the yield of maltose is high relative to other known processes, still the product obtained via the use of such enzymes contains substantial amounts of dextrose and of higher order oligosaccharides (typically having a degree of polymerization (DP) ranging from 3 to about 10). The presence of such other saccharides is undesirable for many purposes, in particular in brewing applications and in maltitol production, and thus expensive chromatographic processes are still required before a high-purity maltose product is obtained. In addition, although it may be feasible to develop new enzymes in an effort to further increase the yield of maltose, such development of new enzymes is extraordinarily expensive, and it is by no means certain that such new enzymes will be more effective than known techniques in preparing maltose products.

For the foregoing reasons, the prior processes for preparation of maltose discussed hereinabove suffer from a number of drawbacks. The present invention seeks to address these drawbacks by providing a process for the production of maltose from starch.

THE INVENTION

It has now been found that the treatment of starch with an enzyme that consists essentially of a beta-amylase enzyme, and which is to the substantial exclusion or complete exclusion of alpha-amylase enzymes and de-branching enzymes, will yield a product mixture that includes maltose and that is substantially free of glucose and of other malto-oligosaccharides having a DP from 3–10. The maltose may be readily separated from the product mixture thus formed via ultrafiltration to yield a high-purity maltose product in which the maltose content is greater than 70% based upon total carbohydrate and in which the combined content of glucose and oligosaccharides having a DP ranging from 3–10 is below 10%. In some embodiments the maltose product prepared via enzymatic hydrolysis content will have a maltose content greater than 70%. Using the invention, a maltose content greater than 85%, more preferably greater than 90%, and even more preferably greater than 95% may be obtained, and in each case, the combined content of glucose and of oligosaccharides having a DP ranging from 3–10 can be kept below about 10%, preferably below about 5%. The production of high purity maltose in accordance with the invention can be very inexpensive relative to known processes. It has further been discovered that the product formed upon enzymatic hydrolysis of the starch may be spray dried to yield a spray dried maltose product.

In accordance with one embodiment of the invention, a starch is treated with an enzyme that consists essentially of a beta-amylase enzyme, and which is to the substantial exclusion or complete exclusion of alpha-amylase enzymes and de-branching enzymes. The starch is so treated under conditions that are suitable for the hydrolysis of the amylose component of the starch to form maltose, and for the hydrolysis of the amylopectin component of the starch to form maltose and at least one higher molecular weight carbohydrate. Generally, the resulting mixture of starch hydrolysis products will comprise maltose and the higher molecular weight carbohydrates to the substantial exclusion of other malto-oligosaccharides. This mixture may itself have a high maltose content, and may easily be resolved via ultrafiltration into a maltose fraction that has a maltose content greater than 70%, in most cases substantially greater. Moreover, because of the substantial absence of other malto-oligosaccharide by-products in the maltose fraction, such as would be present via conventional processes for maltose production, the mixture may be resolved via ultrafiltration, and no column chromatographic process is required. Upon ultrafiltration, most of the maltose passes through the membrane, leaving some maltose in the retentate. If desired, diafiltration may be used to separate substantially all of the maltose from the high molecular weight carbohydrates in the retentate.

In accordance with anther embodiment of the invention, a starch is treated with an enzyme that consists essentially of a beta-amylase enzyme under conditions that are suitable for the hydrolysis of the amylose and amylopectin components of the starch to form maltose and at least one higher molecular weight carbohydrate. After further optional treatments, such as to remove retrograded amylose, the product mixture that is formed is spray-dried. The spray-dried product readily may be transported and processed.

DESCRIPTION OF THE PREFERRED EMBODIMENTS

The invention contemplates the production of maltose from starch. Any suitable starch may be employed in connection with the invention, and thus, for instance, starches such as corn, rice, wheat, tapioca, maize, potato, barley, oat, and, more generally, any starch suitable for enzymatic hydrolysis may be used in connection with the invention. It is not necessary to use a so-called waxy or glutinous starch in connection with the invention, but to the contrary the starch can have any suitable amylose content, such as an amylose content of 10%, 15%, 20%, 25%, or a greater amylose content. It is contemplated that the starch may be a partially derivatized or otherwise modified starch, or may be a starch that has been thinned or enzymatically treated. For instance, a starch that has been lightly oxidized may be employed.

The starch should be liquefied via heat, enzymatic, or acid treatment prior to treatment with the beta-amylase enzyme. Preferably, the starch is liquefied via acid treatment, although low amylose starches may require liquefaction only with heat and may be suitably liquefied at the operating temperature of the enzymatic hydrolysis. Generally, the starch should be liquefied to an extent such that it would remain liquid at the operating temperature of the beta-amylase hydrolysis, but not liquefied to an extent such that the starch is converted to saccharides having so low a degree of polymerization that it is difficult to separate such saccharides from maltose via ultrafiltration. In other words, the degree of liquefaction should be such that, upon enzymatic hydrolysis with the beta-amylase enzyme, the combined content of glucose and oligosaccharides in the DP 3–10 range does not exceed about 10%, and preferably does not exceed about 5%. It has been found acceptable to liquefy the starch to a dextrose equivalent (DE) value of about 2 as measured via conventional techniques. Generally, the DE of the starch should be kept below about 1, and should thus range between 0 and about 1, although it may be difficult to measure the DE with precision in this range. For corn starch, it is preferable that the starch is liquefied in an aqueous solution at a liquefaction temperature ranging from about 220° F. to about 320° F., and for a time ranging from about 5 minutes to about 30 minutes.

The starch solids level preferably ranges initially from about 5% to about 30%, more preferably, from about 15% to about 30%. It is believed that a lower solids level in the starch slurry will result in a higher purity maltose upon enzymatic hydrolysis. While it is not intended to limit the invention to a particular theory of operation, it is believed that a lower solids content requires a lesser degree of liquefaction to attain the desired viscosity range. In the case of dent corn starch, it has been found that a viscosity window of between 25 and 45 centipoise (Norcross Shell Cup) is optimal. In the case of waxy starches, viscosities outside this range may be acceptable. The pH of the starch slurry should be adjusted to a level sufficient to provide controlled acid hydrolysis of the starch in the presence or absence of catalyzing alpha amylase enzymes; most preferably, under a given set of conditions, the variability of the slurry pH should be no more than +/−0.1 pH, with the precise pH value depending upon the starch source, the slurry solids, and the operational conditions of the liquefaction equipment employed. As a practical matter, the pH can vary more widely while still resulting in a satisfactory maltose product. Preferably, the starch liquefaction is monitored via viscosity and adjusted accordingly.

In accordance with one embodiment of the invention, the starch is liquefied with an alpha-amylase enzyme to reduce the molecular weight of the starch, thereby reducing the viscosity of the starch and thereby permitting processing at a higher solids level. Suitable commercial liquefying enzymes may be obtained from Genencor International or from Novozymes A/S. Any suitable liquefaction conditions may be employed. The dosing level of the alpha-amylase enzyme depends upon the desired solids level and the desired maltose purity, and desirably ranges from about 0.005% to about 0.02% of a commercial strength enzyme by dry solids basis starch. In this embodiment, the alpha-amylase enzyme preferably is quenched prior to saccharification via any suitable quenching procedure. For instance, when the starch is liquefied at a temperature less then 250° F. and 5 minutes residence, the alpha-amylase enzyme is quenched by reducing the liqefact pH to less than 4.0 and holding at a temperature of from 180 to 190° F. for at least about 15 minutes.

Upon liquefaction, the liquefact is immediately cooled and the pH is adjusted to the optimum conditions for beta-amylase activity. The starch then is treated with the enzyme under any conditions suitable to result in the hydrolysis of this liquefied starch to form maltose. A preferred enzyme is OPTIMALT BBA, available from Genencor International, Inc. The enzyme may be added in any amount sufficient to achieve this result, but generally, the dosing of the enzyme should be in excess of the minimum viscosity limited conversion of approximately two Genencor International, Inc. OPTIMALT BBA Diastatic Power units per kilogram of starch, the Diastatic Power units being defined as being the amount of enzyme contained in 0.1 ml of a 5% solution of the sample enzyme preparation that will provide sufficient reducing power to reduce 5 ml of Fehling's solution when the sample is incubated with 100 ml of substrate for one hour at 20° C.

The enzymes should be allowed to act on the starch for any amount of time suitable to form maltose. Under the preferred reaction conditions discussed hereinabove, saccharification generally is 90% complete within 4 hours. The optimum temperature and pH of the starch hydrolysis will vary depending on the particular beta-amylase enzyme employed, but typically the temperature will range from about 55° C. to about 65° C. and the pH will range from about 5.0 to about 6.0.

At the conclusion of the enzymatic hydrolysis, a product that contains maltose and at least one higher molecular weight carbohydrate will be provided. Optionally, but preferably, this product mixture is clarified and decolored by any suitable procedure, such as carbon treatment, filtration, centrifugation, and/or precipitation, before it is further processed. Maltose content in the product may be at least about 30% by weight, and in some cases much higher. If the enzyme is allowed to act under optimum conditions for an optimum reaction time, the maltose content of such product may be equal to or greater than about 50%, in some cases equal to or greater than 60%, in some cases equal to or greater than 65%, in some cases greater than or equal to about 70%, and even in some cases equal to or greater than about 75%, while the content of higher molecular weight carbohydrates having a dextrose equivalent value (DE) less than 5 may be greater than about 20%. The combined content of glucose and of oligosaccharides in the DP 3–10 range is below about 10%, and preferably is below 5%.

It is contemplated that in some instances a lower maltose content in the product may be desired. In such case, the enzyme may be quenched prior to the optimum reaction time, such as by adjusting the pH or applying heat. In a highly preferred embodiment, a correlation between enzyme reaction time and resulting maltose content is prepared or is provided in advance. Such a correlation between reaction time and maltose content may be determined empirically, for instance, by performing at least two experiments in which the enzyme is quenched at different reaction times each less than the optimum reaction time, and measuring the maltose content in each case. Once the correlation has been prepared or provided in advance, a desired maltose content may be obtained by quenching the enzyme after a reaction time determined with reference to the predetermined correlation. It is also contemplated that the maltose content may be controlled by conducting the liquefaction under less than optimal conditions, although such is not preferred inasmuch as a higher content of glucose and/or lower molecular weight sugars in the product mixture may thereby result. In accordance with this embodiment of the invention, various products having differing maltose contents can be prepared. For instance, it is contemplated that a product in which the maltose content is 10%, 20%, or 30% may be prepared. In each case the combined content of glucose and of oligosaccharides in the DP 3–10 range can be kept below about 10%, and preferably below 5%.

Retrograded amylose may be found as a by-product of the enzymatic hydrolysis. In accordance with one embodiment of the invention, at least some of the retrograded amylose is separated from the product mixture. For instance, the saccharified solution may be maintained at a temperature below about 140° F. to allow at least a portion of the retrograded amylose to crystallize. The crystallized amylose then may be separated from the saccharified starch mixture by any suitable technique, such as via microfiltration, by which is contemplated separation at a resolution sufficient to separate the retrograded amylose but not sufficient to separate maltose from higher molecular carbohydrates in the product mixture. Alternatively, the retrograded amylose may be separated via centrifugation, using any technique known in the art or otherwise found to be suitable.

In accordance with one embodiment of the invention, a high purity maltose product is separated from the product mixture. Most preferably, a maltose product is separated from the product mixture via ultrafiltration of the product mixture, by which is contemplated separation of the maltose from higher molecular weight carbohydrates using a membrane or other suitable separation medium that is effective for this purpose. Generally, a membrane having a molecular weight cut off (MWCO) of 10,000 or less, preferably a MWCO of 5000 or less, is suitable. Suitable commercially available membranes available from Sydnar Filtration and from Osmonics De Sal. Upon ultrafiltration, the permeate includes a high purity maltose liquid, which may be evaporated to a high solids content (greater than 55%) that crystallizes upon cooling. The purity of the maltose obtained upon crystallization can be as high as 98%, with dextrose levels below the detection level of conventional HPLC analysis. The retentate typically will include a higher molecular weight carbohydrate having a DE less than 5 and some retained maltose. If desired, the retentate may be diafiltered to recover additional maltose by flushing the filter with excess water.

In accordance with another embodiment of the invention, the product mixture obtained upon enzymatic hydrolysis of the starch is spray-dried. Surprisingly, it has been found that it is possible to spray dry a maltose product prepared as discussed hereinabove. While it is not intended to limit the invention to a particular theory of operation, it is believed that the composition of the product is especially suitable for spray drying, perhaps because of the relatively low amount of maltotriose, which is substantially more hygroscopic than maltose. The high molecular weight carbohydrate in the product may function as an effective spray drying enhancer. Prior to spray drying, the product mixture may be clarified and decolored, and retrograded amylose may be removed as discussed above.

Carbohydrate percentages given herein are expressed on a dry solids basis per total carbohydrate weight.

The following examples are provided to illustrate the invention, but should not be construed as limiting in scope.

EXAMPLE 1

This Example illustrates the preparation of maltose from waxy corn starch.

Starch from waxy corn was made to an aqueous slurry containing 12 to 15% solids and pH 6.0 to 7.0. The slurry was then liquefied by jet cooking through a Hydro Thermal Jet (Model #M103-030) at 300° F., 60 to 65 psi with a 5 minute residence time at 300° F., 50 to 55 psi. The liquefact was immediately cooled, the pH was adjusted to 5.5 with hydrochloric acid, and dosed with beta-amylase. Using a commercial barley beta-amylase enzyme (Genencor International, Inc. OPTIMALT BBA), dosing was 6.15 DP units per kilogram of starch or 0.05 wt. % grams of liquid enzyme per gram of dry starch. Saccharification was performed at 140° F. for 4 to 24 hours. The solution was then separated by ultrafiltration through a polysulfone 3000 MWCO membrane (Syndar Filtration). The permeate, containing approximately 6% solids, was then evaporated to 70% solids which contained not less than 95% maltose. The malto-oligosaccharide content in the permeate solution was evaluated by HPLC using a Phenomenex Rezex-RSO-oligosaccharide/Silver column with RI detection and found to be as follows:

| DP1 | Maltose | DP3 | >DP3 |
|---|---|---|---|
| 0.2% | 97.9% | 0.4% | 1.4% |

As seen, the invention provided a maltose product of extremely high purity, with only about 2% glucose and saccharides having a DP greater than 3.

EXAMPLE 2

This Example illustrates the preparation of maltose from wet mill processed yellow dent corn starch under various liquefaction conditions.

Dent corn starch was liquefied under various reaction conditions, as given in the following Table. The pH of the starch was adjusted where necessary, and then was saccharified with a beta-amylase enzyme as in Example 1. Samples then were filtered through a 3000 MWCO membrane and analyzed as in Example 1, yielding the results reported in the Table below.

| Example | % solids | pH | Temp (F.) | Residence Time (min) | Dextrose | Maltose | DP3 | Higher DP |
|---|---|---|---|---|---|---|---|---|
| 2A | 15 | 3.5 | 300 | 5 | 0.3 | 96.4 | 0.8 | 3.2 |
| 2B | 20 | 3.0 | 300 | 5 | Nd | 96.0 | 1.2 | 2.8 |
| 2C | 20 | 2.75 | 300 | 5 | Nd | 89.9 | 2.2 | 7.9 |
| 2D | 25 | 2.75 | 300 | 5 | Nd | 93.8 | 2.2 | 4.0 |
| 2E | 25 | 3.0 | 300 | 20 | Nd | 89.4 | 2.9 | 7.7 |
| 2F | 25 | 2.75 | 300 | 20 | 1.2 | 84.8 | 4.6 | 9.4 |
| 2G | 30 | 3.0 | 300 | 20 | Nd | 91.6 | 3.7 | 4.7 |
| 2H | 30 | 2.75 | 300 | 20 | 1.3 | 84.9 | 4.8 | 9.0 |
| 2I | 30 | 3.0 | 300 | 20 | Nd | 92.3 | 2.9 | 4.8 |
| 2J | 30 | 3.0 | 280 | 20 | Nd | 92.5 | 2.5 | 5.0 |

Nd = not detected

All of the examples provided a very high purity maltose product, with even Example 2F providing a higher purity product than is obtainable conventionally without chromatographic separation.

EXAMPLE 3

This Example illustrates the liquefaction of wet mill processed yellow dent corn starch with an alpha-amylase enzyme.

In two separate runs, starch from wet mill processed yellow dent corn was adjusted to a solids content of 12 or 25% dry solids basis and the pH was adjusted to pH 5.50 with hydrochloric acid. Each starch slurry was then dosed with a liquefying alpha-amylase enzyme (Novo TERMAMYL SC) to 0.005–0.02% dry solids basis. The slurries were then jet cooked at 230° to 290° F. with a 5 to 20 minute residence. The alpha-amylase then was quenched by reducing the liquefact pH to less than 4.0 and holding at 180 to 190° F. for 15 minutes. The liquefacts then were saccharified with a beta-amylase enzyme, then filtered and evaporated as in Example 1.

This procedure was followed for the following reaction conditions, yielding the following products.

| 12% solids, 0.01% dsb Termamyl SC, 270° F./20 min, 4% solids product ||||
| --- | --- | --- | --- |
| DP1 | Maltose | DP3 | >DP3 |
| 0% | 96.6% | 0.5% | 2.9% |

| 25% solids, 0.2% dsb Termamyl SC, 230° F./5 min, acid kill, 18% solids product ||||
| --- | --- | --- | --- |
| DP1 | Maltose | DP3 | >DP3 |
| 0% | 88.3 | 4.3 | 7.4 |

The later example provided a maltose content of 88.3%, which, while lower than that for some of the previous examples, was higher than that conventionally attainable.

EXAMPLE 4

This Example illustrates crystallization of retrograded amylose from the saccharified starch mixture.

This saccharified solution from Example 2 was held at 130° F. for 18 to 24 hours. This hold time was necessary for the slow, complete formation of amylose crystals. This saccharified mixture was then pre-filtered through a minimal microfilter of porosity 0.1 to 0.8 micron (U.S. Filter ceramic membranes). The filtration was performed at temperatures not greater than 140° F. to maintain the insoluble retrograded amylose. The filter pore size was selected to produce maximum flux with minimum turbidity in the permeate. For a process using 15% dry solids starch feed at pH 3.5, a 0.8 micron filter will adequately clarify the feed material.

The retentate from the pre-filtration was enriched in the amylose faction and the permeate contained maltose and high molecular weight carbohydrates. Analysis of the amylose particle size using a Malvern Instruments Ltd. Mastersizer showed that 90% of the amylose crystals were of a size between 1 and 20 microns. The crystal size distribution appears to broaden and decrease in size as the process increases in solids and decreases in pH. At a 25% solids content and pH of 3.0, a 0.1 micron filter is necessary for minimal clarification.

The permeate from the microfiltration step was then ultrafiltered as previously described to generate a high purity maltose product.

EXAMPLE 5

This Example illustrates recycling of a high molecular weight carbohydrate fraction.

The retentate obtained from Example 2 was recycled and blended with wet milled starch to a solids content of 12 to 14% at a ratio of 3:2 retentate solids to starch solids and processed as described in Example 2, with the saccharification step being kept to 4–5 hours. The maltose permeate obtained upon ultrafiltration was analyzed and found to have the following composition:

| DP1 | Maltose | DP3 | >DP3 |
| --- | --- | --- | --- |
| 0.4% | 96.5% | 0.7% | 2.4% |

As seen, a high purity maltose product was provided.

EXAMPLE 6

This Example illustrates that various membranes may be used in the ultrafiltration of maltose from the product formed upon enzymatic saccharification.

Material was processed through the microfiltration step as described in Example 4. Laboratory scale samples were processed on a hollow fiber unit from A/G Technology Corp. (AGT UFP-3-C-4A 3000 NMWC). This filter was run with a Masterflex peristaltic pump (model 7553-70) with a Masterflex head (model 70 15-52) connected with Norprene tubing (model 6402-15). Recirculation rates were adjusted to maintain pressures between 10 psi and 20 psi.

Large scale samples were tested on commercially available spiral wound elements installed and operated on a NIRO Inc. Model R16 Single Stage UF/RO Pilot Plant. Elements evaluated were purchased from Syndar Filtration (PES 3000 MWCO VT2B3838) or Osmonics De Sal (GH/G-10, GK/G-20 and GM/G-50 3838). Operating conditions were those specified by the membrane manufacturer.

Permeate was sampled and analyzed by HPLC. Results are averages from multiple permeate samples.

| Membrane | MWCO | Solids | DP1 | Maltose | DP3 | DP>3 |
| --- | --- | --- | --- | --- | --- | --- |
| AGT 3000 | 3000 | 25 | Nd | 93.8 | 2.2 | 4.0 |
| Syndar 3000 | 3000 | 14 | 0.1 | 97.2 | 0.6 | 2.187 |
| Desal G10 | 2500 | 25 | Nd | 96 | 0.65 | 3.3 |
| DeSal G20 | 3500 | 25 | Nd | 97.4 | 1.5 | 1.2 |
| DeSal G50 | 8000 | 25 | Nd | 96.5 | 1.5 | 2.0 |

EXAMPLE 7

This Example demonstrates the ability to spray dry maltose syrups of various compositions.

Maltose syrup was prepared as described in Example 2 using a 15% dsb starch feed. Three compositions were evaluated, including the ultrafilter feed material that contained 65% maltose and 35% high molecular weight carbohydrate material having a DE less than 5 (the "65/35 material"), the ultrafilter permeate material that contained 95% maltose and 5% high molecular weight carbohydrate (the "95/5 material"), and a blend of these materials that contained 90% maltose and 10% high molecular weight carbohydrate (the "90/10 material"). These solutions were spray dried on a Yamoto-Ohkawara Spray Dryer DL-41 with a 2850-SS nozzle and a 65-5 SS orifice. Operating conditions were: drying air 0.75 m³/min, atomizing air 0.25 Mpa, feed rate 20 ml/min, inlet temperature 300° C. outlet temperature 100° C. The feed solids were from 6% to 30% dsb for the 65/35 and 90/10 material. The dry powder produced from these two products contained moisture content of 2–3%. The 95/5 material melted in the receiver line at these temperatures but was effectively dried at reduced temperature of 200° C. inlet temperature, 80° C. outlet temperature with a resulting moisture content of 2.5%.

EXAMPLE 8

This Example describes a scale-up pilot production of high purity maltose.

A commercial yellow dent starch available from Grain Processing Corporation of Muscatine, Iowa (B 200) was slurried to a solids level of 15% dsb and a pH of 3.5 with hydrochloric acid. The slurry was fed at a rate of 2 gpm through a Hydroheater jet Series M103 AS at a pressure of 60 psi and a temperature of 300° F. The post-jet residence time was 7.5 minutes resulting in a primary liquefact of a Shell Cup viscosity (Norcross Corp.) of 25 cp. The pH of the liquefact was continuously adjusted to 5.5 with soda ash and cooled through a heat exchanger to 140° F. The liquefact was dosed with Spezyme BBA (Genencor International, Inc.) at a level of 0.05% dsb and converted at temperature through an 8-stage plug flow reactor with continuous agitation and a total residence time of eight hours. The saccharified product was clarified by passing the product through a NIRO Model-C ceramic filtration unit with a 19-element Membrelox, 0.8 um ceramic bundle. The clarified permeate was then ultrafiltered through a NIRO Model-U ultrafiltration unit containing DeSal G-50 membranes. Ultrafiltered permeate was collected, evaporated to 70% solids and stored in 50 pound lots. Twelve lots were sampled and assayed for maltose purity by HPLC and ion content by Dionex ion chromatography. The following table summarizes those results.

| Analysis | Average | Std. Dev. |
| --- | --- | --- |
| % DP1 | Nd | |
| % DP2 | 97.54 | 0.87 |
| % DP3 | 0.96 | 0.15 |
| % higher | 1.51 | 0.79 |

| Analysis | Average | Analysis | Average |
| --- | --- | --- | --- |
| Li ppm | 0 | F ppm | 27.17 |
| Na ppm | 187.8 | Cl ppm | 1691.00 |
| NH4 ppm | 0.8 | NO2 ppm | 18.50 |
| K ppm | 44 | NO3 ppm | 67.33 |
| Mg ppm | 250.4 | SO4 ppm | 671.00 |
| Ca ppm | 1023 | PO4 ppm | 69.67 |

As seen, a maltose product having a very high purity was produced. No glucose was detected, and the total content of sugars in the DP 3–10 range was very low.

EXAMPLE 9

This Example describes the production of a 75% maltose syrup low in dextrose and maltotriose.

A commercially available yellow dent corn starch was slurried to a solids content of 25% dsb and a pH of 3.0 with hydrochloric acid. The slurry was liquefied at 300° F. on a lab scale reactor as described in Example 1 with a 7.5 minute residence time resulting in a liquefact of Shell Cup viscosity of 21 cp. The liquefact was cooled to 140° F., the pH was adjusted to 5.5 with soda ash, and was dosed with Spezyme BBA at 0.5% dsb as previously described. After an 8-hour hold at 140° F., the saccharified product was microfiltered on a NIRO Model-R unit using a Membralox 0.1 um ceramic filter. The permeate was at 17% solids and spray dried on a 60 inch pilot scale spray dryer with a SC 43 nozzle, at a feed pressure of 2000 psi, inlet temperature of 510–550 F., outlet temperature 250F. The product was analyzed by HPLC.

As a control, two commercially available maltose syrups were analyzed via HPLC. The following table shows the results of the analyses of each product.

| Sample ID | Example 9 | Commercial syrup A | Commercial syrup B |
| --- | --- | --- | --- |
| DP1 | 0.7 | 1.6 | 2.0 |
| DP2 | 74.6 | 72.3 | 63.1 |
| DP3 | 2.5 | 18.7 | 17.9 |
| DP4 | 0.2 | 0.3 | 0.5 |
| DP5 | 0 | 1.1 | 0.2 |
| DP6 | 0 | 2.1 | 1.6 |
| DP7 | 0 | 0.8 | 1.3 |
| DP8 | 0 | 0.6 | 2.8 |
| DP9 | 0.3 | 0.3 | 1.4 |
| DP10 | 0.2 | 0.1 | 0.7 |
| Higher DP | 21.5 | 2.1 | 8.6 |

The DP profile of the maltose product prepared in accordance with Example 9 was markedly different from that of the commercially available syrups. As seen, the product of Example 9 had a much lower maltotriose (DP3) content than either of the commercial syrups.

It is thus seen that the invention provides a process for preparing a high purity maltose product. The product can be prepared without chromatographic separation to yield a product that has a very low content of glucose and malto-oligosaccharides having a DP ranging from 3–10.

While particular embodiments of the invention have been shown, it will be understood that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention. All references and pending applications cited herein are hereby incorporated by reference in their entireties. U.S. patent application Ser. No. 09/795,996, filed Feb. 28, 2001 by Richard L. Antrim and Clark Lee and assigned attorney docket number 209498, also is hereby incorporated by reference.

What is claimed is:

1. A method for preparing a maltose product, comprising:
    treating a starch with an enzyme that consists essentially of a beta amylase enzyme under conditions suitable to form a product mixture that includes maltose and at least one higher molecular weight carbohydrate, said starch containing amylose in an amount of 10% or greater, whereby at least a portion of said amylose becomes retrograded;
    allowing at least a portion of said retrograded amylose to crystallize from said product mixture;
    separating the crystallized retrograded amylose from said mixture leaving a remaining mixture containing maltose and a higher molecular weight carbohydrate having a dextrose equivalent value of less than 5; and
    recovering a maltose product from said remaining mixture thereby leaving a second fraction, said maltose product containing relatively more maltose than said second fraction.

2. A method according to claim 1, further comprising liquefying said starch with an alpha-amylase enzyme; and quenching said alpha amylase enzyme prior to treating said starch with said beta-amylase enzyme.

3. A method according to claim 1, said maltose product comprising at least 85% maltose by weight by dry solids basis.

4. A method according to claim 1, said maltose product comprising at least 90% maltose by weight by dry solids basis.

5. A method according to claim 1, said maltose product comprising at least 95% maltose by weight by dry solids basis.

6. A method for preparing a spray-dried maltose product, comprising:

treating a starch with an enzyme that consists essentially of a beta-amylase enzyme under conditions suitable to form a product mixture that includes maltose and at least one carbohydrate of higher molecular weight than maltose and that further includes retrograded amylose;

allowing at least a portion of said retrograded amylose to crystallize from said product mixture; and spray-drying said product mixture.

7. A method according to claim 6, said starch having an amylose content of 10% or greater.

8. A method according to claim 7, said starch comprising dent corn starch.

9. The method according to claim 6, further comprising liquefying said starch prior to treating said starch with said beta-amylase enzyme.

10. The method according to claim 6, further comprising liquefying said starch with an alpha-amylase enzyme; and quenching said alpha-amylase enzyme prior to treating said starch with said beta amylase enzyme.

11. A method according to claim 6, said maltose being present in said product in an amount of least 70% by weight by dry solid basis prior to separation of said retrograded amylose.

12. A method according to claim 1, said starch having at least 20% amylose content.

13. A method according to claim 6, said starch having at least 20% amylose content.

14. A method according to claim 6, the method further comprising the step of separating the crystallized retrograded amylose from said product mixture prior to spray drying said product mixture.

* * * * *